United States Patent [19]
Arkles

[11] Patent Number: 5,874,603
[45] Date of Patent: Feb. 23, 1999

[54] BRANCHED HIGHER ALKYLSILANES

[75] Inventor: Barry C. Arkles, Dresher, Pa.

[73] Assignee: Gelest, Inc., Tullytown, Pa.

[21] Appl. No.: 892,595

[22] Filed: Jul. 15, 1997

[51] Int. Cl.$^6$ .................................. C07F 7/08; C07F 7/18
[52] U.S. Cl. .......................... 556/465; 556/400; 556/430; 556/450; 556/489
[58] Field of Search ..................................... 556/465, 489, 556/430, 400, 450

[56] References Cited

U.S. PATENT DOCUMENTS 5,710,301  1/1998  Fujiki ...................................... 556/465

OTHER PUBLICATIONS

Csaba Horváth, "Reversed Phase Chromatography With Alkyl–Silica Stationary Phases," D.E. Leyden et al., *Silylated Surfaces* (1980), pp. 269–300.

S.A. Wise et al., "Investigations of Selectivity In Reversed-–Phase Liquid Chromatography On Chemically Bonded $C_{18}$ Phases," D.E. Leyden *Silanes Surfaces Interfaces* (1986), pp. 349–370.

"C20–C24 Alpha Olefin Fraction," Product Data Sheet of Chevron, Houston, TX (1993).

"C24–C28 Alpha Olefin Fraction," Product Data Sheet of Chevron, Houston, TX (1993).

"1–Octadecene," Product Data Sheet of Chevron, Houston, TX (1993).

Van Der Voort et al., "Silylation Of The Silica Surface A Review," *J. Liq. Chrom. & Relat. Technol.*, vol. 19, Issues 17 & 18 (1996), pp. 2723–2752.

*Primary Examiner*—Paul F. Shaver
*Attorney, Agent, or Firm*—Panitch Schwarze Jacobs & Nadel, P.C.

[57] ABSTRACT

A branched alkylsilane includes a branched hydrocarbon backbone which has a linear or branched alkylsilyl moiety extending asymmetrically from the backbone such that the backbone has a first portion and a second portion extending from the moiety. The second portion has two carbon atoms more than the first portion, and the alkylsilyl moiety includes at least one hydrolyzable group bound to silicon for reacting with a substrate. A method for preparing a branched alkylsilane useful for chromatographic applications includes the steps of preparing a vinylidene olefin by dimerization of an α-olefin and reacting it with a monomeric silane having a silicon-hydrogen bond in the presence of a metallic catalyst such that the silicon-hydrogen bond is added to the vinylidene double bond of the vinylidene olefin thereby converting the double bond to a single bond and bonding the silicon of the monomeric silane to the vinylidene olefin to form a branched alkylsilane.

19 Claims, No Drawings

BRANCHED HIGHER ALKYLSILANES

BACKGROUND OF THE INVENTION

Liquid phase chromatography and extraction techniques are dependent on the interaction of a region bonded to a solid support, such as silica, and a solvent environment containing solutes of interest. The support is stationary with respect to the liquid or solvent phase. The interacting region is designated as the bonded phase or interphase. A general overview of this technology may be found in C. Horvath, *Silylated Surfaces* (1980), p. 269. Features which contribute to a successful bonded phase include reproducible, non-bonding interactions with solutes in the mobile phase under a variety of operating conditions, such as temperature, pressure, the nature of the solvent and the stability of the interaction over a period of time.

The most widely used of such bonded phases is a hydrophobic phase which may be derived from octadecyl functional silanes. For example, octadecyldimethylchlorosilane- and octadecyltrichlorosilane-treated silica are the most widely used bonded phases for high pressure liquid chromatography (HPLC) and solid phase extraction, respectively. These compounds terminally bond to the silica using a Si—O—Si bond.

In general longer, extended chain length is desirable to provide more interaction of the chain with the material of interest such as the solute. However, octadecyl (C18) has been considered a natural limit for two principle reasons. First, as linear chain length increases, chain folding is induced, particularly when the mobile phase is polar, such as water/acetonitrile combinations. The chain folding process reduces the ability of the bonded phase to interact with the material of interest. In the extreme case, crystallization of the bonded phase occurs resulting in minimal interaction. Second, difficulty is encountered in obtaining pure, higher olefins at practical economics. The oligomerization process for higher α-olefins produces mixtures which are increasingly difficult to purify at higher molecular weights, with α-olefins of a length greater than twenty carbon atoms available at purity levels of only about 50%. As such, for practical purposes, the highest number olefin used for chromatographic and extraction purposes is an 18 carbon atom chain length. Information concerning the hydrosilylation of olefins may be found in the textbook entitled, B. Marciniec, ed., *Comprehensive Handbook on Hydrosilylation* (1992).

As such, there is a need in the art for a material for forming an improved bonded phase which has increased bonded phase interaction while minimizing the effect of chain folding and protecting the Si—O—Si bond between the silanes and the support from hydrolytic attack. Further, there is a need for a simple synthesis reaction for forming an alkylsilane having a relatively long chain length with a high level of purity for use in a bonded phase.

BRIEF SUMMARY OF THE INVENTION

The invention includes a branched alkylsilane which comprises a branched hydrocarbon backbone having a linear or branched alkylsilyl moiety extending asymmetrically from the backbone such that the backbone has a first portion and a second portion extending from the alkylsilyl moiety. The second portion has two carbon atoms more than the first portion. The alkylsilyl moiety comprises at least one hydrolyzable group bound to silicon for reacting with a substrate.

The invention also includes, in one embodiment, a branched alkylsilane which comprises a branched aliphatic hydrocarbon backbone having a linear or branched alkylsilyl moiety extending asymmetrically from the backbone such that the backbone has a first portion and a second portion extending from the alkylsilyl moiety. The second portion has two carbon atoms more than the first portion. The alkylsilyl moiety comprises at least one hydrolyzable group bound to silicon for reacting with a substrate. The branched alkylsilane has formula (I):

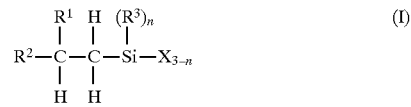

wherein $R^1$ is the first portion of the hydrocarbon backbone and is a substituted or unsubstituted alkyl chain of m carbon atoms; m being an integer such that $18 \geq m \geq 6$; $R^2$ is the second portion of the hydrocarbon backbone and is a substituted or unsubstituted linear or branched alkyl chain having m+2 carbon atoms; $R^3$ is a substituted or unsubstituted linear or branched alkyl chain of from 1 to 4 carbon atoms; n is from 0 to 2; and X is a group selected from the group consisting of alkyl, halogen, alkylamine, dialkylamine, and alkoxy.

The invention also includes a treated substrate for use in chromatographic applications, which comprises a substrate and a branched alkylsilane comprising a branched hydrocarbon backbone having a linear or branched alkylsilyl moiety extending asymmetrically from the backbone such that the backbone has a first portion and a second portion extending from the alkylsilyl moiety. The second portion has two carbon atoms more than the first portion. The silicon in the alkylsilyl moiety is bound to the substrate by an oxygen atom such that the first portion and the second portion of the backbone extend outwardly from the substrate for providing a bonded phase useful for reproducible molecular interaction.

A method for preparing a branched alkylsilane useful for chromatographic applications is also included within the present invention. The method comprises the steps of preparing a vinylidene olefin by dimerization of an α-olefin, and reacting the vinylidene olefin and a monomeric silane having a silicon-hydrogen bond in the presence of a metallic catalyst such that the silicon-hydrogen bond is added to the vinylidene double bond of the vinylidene olefin thereby converting the vinylidene double bond to a single bond and bonding the silicon of the monomeric silane to the olefin to form a branched alkylsilane having a first portion and a second portion extending from an alkylsilyl moiety. The second portion has two carbon atoms more than the first portion.

A method for forming a bonded phase for use in chromatographic applications is also within the scope of the present invention. The method comprises the steps of forming a branched alkylsilane comprising a hydrocarbon backbone and a linear or branched alkylsilyl moiety having at least one hydrolyzable leaving group bound to silicon and extending asymmetrically from the backbone such that the backbone has a first portion and a second portion extending from the alkylsilyl moiety. The second portion has two carbon atoms more than the first portion. The branched alkylsilane is reacted with a substrate comprising silicon in the presence of a hydroxy-containing compound to form a Si—O—Si bond between the silicon of the alkylsilyl moiety and the silicon of the substrate.

DETAILED DESCRIPTION OF THE INVENTION

Certain terminology is used herein for convenience only and is not to be taken as a limitation on the present invention.

As used herein, "branched" means anything other than a straight chain molecule. As used herein, "aliphatic" means an organic compound which does not contain an aromatic ring. "Aromatic" means an organic compound containing benzene or a benzene-derived ring having a resonance structure. "Hydrolyzable" means capable of being hydrolyzed by the presence of water or an —OH containing species. As used herein, "substituted" means an organic or hydrocarbon structure in which one or more of the bonds or atoms is replaced by a substituent group such as linear or branched functional groups, alkyl groups, ionic groups and the like.

The following describes preferred embodiments of the invention. However, it should be understood, based on this disclosure, that the invention is not limited by the preferred embodiments described herein. The invention includes a branched alkylsilane compound, monomeric in nature, which has a hydrocarbon backbone. The backbone is preferably aliphatic, but can include aromatic groups within the chain. Further, the backbone may include various functional groups or substituted groups for specific applications as long as the primary backbone maintains a substantially linear character and the alkylsilyl moiety is located as described herein.

The backbone has an alkylsilyl moiety extending asymmetrically from the backbone, i.e., the number of carbon atoms in the primary chain of the backbone is not equal on either portion extending from the moiety. If the backbone has functional groups or branched sections, the number of carbons for determining location of the alkylsilyl moiety are only those carbons which are in the primary backbone chain, exclusive of the carbon atoms which may lie in functional, substituted or branched groups.

The alkylsilyl moiety may be linear or branched, and is preferably a linear moiety having substituted and/or hydrolyzable groups attached thereto as discussed further below. The alkylsilyl moiety is situated along the backbone such that the hydrocarbon backbone is effectively divided into a first portion and a second portion. As noted above, it is preferred that the alkylsilyl moiety is located asymmetrically on the hydrocarbon backbone, such that the first and second portions of the backbone preferably have an unequal number of carbon atoms in their respective primary chains. More preferably, the second portion has two carbons more than the first portion. The first portion preferably has at least six carbon atoms. This position can be effected by using vinylidene olefins in accordance with the reactions and starting materials described further below.

In the preferred embodiment, the alkylsilyl moiety has at least one, and preferably from one to three, hydrolyzable groups bound to the silicon atom which is situated along the primary chain of the alkylsilyl moiety. The hydrolyzable group(s) should be capable of reacting with a given substrate. As such, the group(s) may be varied or functionalized for use with a particular substrate. In the preferred embodiment discussed herein, for use in chromatographic applications, the preferred substrate includes silica. Other possible preferred substrates, including mullite, zircon and titania, may be used as well as other similar substrates. Particularly preferred hydrolyzable groups which may be used for reacting with a silicon-containing substrate include halogens such as chlorine, fluorine, bromine and iodine; alkylamines and dialkylamines such as methylamine, ethylaamine, propylamine, isopropylamine, butylamine, isobutylamine, pentylamine, hexylamine, dimethylamine, diethylamine, methylethylamine, dipropylamine, methylpropylamine, ethylpropylamine, and similar compounds; and alkoxy groups such as methoxy, ethoxy, propoxy, isopropoxy, butoxy and the like. Preferably, the hydrolyzable group(s) is chlorine, an alkylamine and/or dialkylamine. It will be understood, based on this disclosure, that other hydrolyzable groups having similar properties may be used or other groups may be selected for non-silicon-containing substrates, within the scope of this invention.

While at least one such hydrolyzable group is preferably bound to the silicon atom along the primary chain of the alkylsilyl moiety, other substituted group(s), such as functionalized groups, ionic groups, or other organic or inorganic groups may be bound to the hydrocarbon portion which is bound to the silicon or attached to the primary alkylsilyl chain to achieve desired properties, particularly if the branched alkylsilane is used as a bonded phase for chromatography. One of ordinary skill in the art, would understand based on this disclosure, that such groups can be changed or modified without departing from the spirit of this invention.

Preferably, the alkylsilyl moiety has an alkyl chain portion which is a lower alkyl of from 1 to 4 carbon atoms measured along the primary alkylsilyl chain, such as methyl, ethyl, propyl, isopropyl and the like. Most preferably, the alkylsilyl moiety is an ethylsilyl. The silicon atom is preferably located terminally along the chain to serve as a point of attachment and for reacting with a substrate such that the first and second portions of the backbone would extend outwardly from the substrate after bonding.

The branched alkylsilane as described above, preferably has the following formula (I):

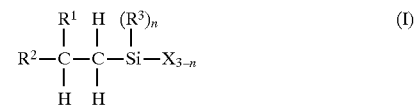

wherein $R^1$ is the first portion and $R^2$ is the second portion of the hydrocarbon backbone. In formula (I) above, $CHCH_2Si(R^3)_nX_{3-n}$ represents the alkylsilyl moiety bound to both $R^1$ and $R^2$. $R^1$ and $R^2$ are preferably both substituted or unsubstituted alkyl chains which may be functionalized or may include various substituted groups as described above with respect to the hydrocarbon backbone. $R^1$ preferably has a chain length along the primary chain of the hydrocarbon backbone which has m carbon atoms, wherein m is an integer such that $18 \geq m \geq 6$. $R^2$ preferably has a chain length along the primary chain of the hydrocarbon backbone which has m+2 carbon atoms. $R^3$ is preferably a substituted or unsubstituted linear or branched alkyl group of from 1 to 4 carbon atoms; n is from 0 to 2, such that the number of hydrolyzable group(s) X and the number of group(s) $R^3$ total three. The hydrolyzable group(s) X may be any of those described above, and preferably is halogen, alkylamine, dialkylamine and/or alkoxy.

A branched alkylsilane as described above, and preferably as represented by formula (I) may be formed by any acceptable chemical reaction pathway. However, it is preferred that the branched alkylsilane is formed by a hydrosilylation reaction of a vinylidene olefin and a monomeric silane. Hydrosilylation can be performed by free radical initiation brought about by heat, peroxides or irradiation. However, it is preferred that the hydrosilylation be carried out in the presence of a metallic catalyst. In hydrosilylation, the addition of a silicon-hydrogen bond to a carbon-carbon double bond, the vinylidene bond, in the olefin converts the double bond as shown below in formula (II) to a single bond as shown below in reaction formula (IV) and attaches the silicon of the monomeric silane in place of the double bond.

Catalysts which may be used to facilitate such a hydrosilylation reaction include platinum complex catalysts such as platinum-divinyltetramethylsiloxane complex, platinum-cyclovinylmethylsiloxane complex, platinum-tetramethyldisiloxane complex, chloroplatinic acid, chloroplatinic acid complexes and/or solutions, and tris-triphenyl phosphine rhodium chloride. More preferably, the hydrosilylation catalyst is platinum-divinyltetramethyldisiloxane complex.

Suitable vinylidene olefins may be formed by any suitable reaction. Preferably, such vinylidene olefins are formed by contacting an α-olefin of at least 8 carbon atoms with a suitable olefin polymerization catalyst to form a vinylidene olefin. While less than 8 carbon atoms is acceptable in accordance with the present invention, it is preferred that at least 8 are used to provide a vinylidene olefin for forming a bonded phase branched alkylsilane in accordance with the present invention which has sufficient molecular interaction capability. Olefins which may be used for forming vinylidene olefins according to the present invention preferably include alkenes of at least 8 carbon atoms. Most preferably, the alkenes are from 8 to 20 carbon atoms, for example, 1-octene, 1-nonene, 1-decene, 1-undecene, 1-dodecene, 1-tridecene, 1-tetradecene, 1-pentadecene, 1-hexadecene, 1-heptadecene, 1-octadecene, 1-nonadecene, 1-eicosene, and similar alkenes. Preferred alkenes include 1-dodecene, 1-hexadecene and 1-tetradecene. Because short or long chains can be used for forming the vinylidene olefins used in the present invention, problems encountered in achieving high-purity in the synthesis of high molecular weight, long chain α-olefins for bonded phase use are minimized. Long chain olefins can be used in the present invention, however, they are not necessary because shorter olefin chains of high purity may be dimerized to substantially increase bonded phase interaction while maintaining purity in a simple synthesis reaction. Lower vinylidene olefins have been made by Chevron, Olefins & Derivatives Division, Houston, Tex. and a process for making them is described in Great Britain Patent No. 775,384 of Ziegler. While larger vinylidene olefins are of interest and have been studied, applicants have not found a commercial source for long chain vinylidene olefins.

Olefin polymerization catalysts are known in the art, such as the Ziegler-Natta-type, or other organo-metallic complexes including triethylbutylaluminum, triethylaluminum and other similar catalysts, and need not be described in detail herein. Once the reaction is complete, the catalyst should be neutralized by the appropriate agent, typically a base or hydrolytic compound, and the product is purified by filtration or by any other suitable means known in the art.

The vinylidene olefins used in the reaction for forming a branched alkylsilane according to the present invention are preferably of the following formula (II):

wherein $R^1$ and $R^2$ are as described above, with $R^2$ preferably being an alkyl group of at least 8, and more preferably from 8 to 20 carbon atoms, R preferably being an alkyl group of at least 6 carbon atoms, and more preferably from 6 to 18 carbon atoms, and $R^2$ having two carbon atoms greater than $R^1$. Such a dimer structure provides a vinylidene double bond extending from a branched chain configuration which is capable of undergoing hydrosilylation by an alkylsilane.

A vinylidene olefin, as described above, is reacted with an alkylsilane having the desired functional, substituted and/or hydrolyzable groups bound to a silicon atom in the primary chain of the alkylsilane. Preferably a hydrogen atom is bound to the silicon atom, and the silicon atom displaces the double bond of the vinylidene olefin.

The monomeric silanes may be a silane or alkylsilane having at least one silicon atom. Preferably, the silicon atom is bound to hydrogen. Other functional groups, substituted groups and hydrolyzable groups may be added to silicon. A total of three such groups may be provided. The alkylsilane preferably has the following formula III:

wherein $R^3$, X and n are as defined above with respect to formula (I). It should be understood, based on this disclosure, that the monomeric silane may be varied to provide different alkylsilyl moieties to the branched alkylsilane. In addition, the reaction between the alkylsilane and the vinylidene olefin may occur by different pathways. One method for synthesizing the branched alkylsilanes includes converting the vinylidene olefin to a halide, forming a Grignard reagent from the halide, and then carrying out a subsequent displacement reaction using a suitable halosilane. However, the preferred reaction for forming a branched alkylsilane in accordance with the present invention is represented as follows:

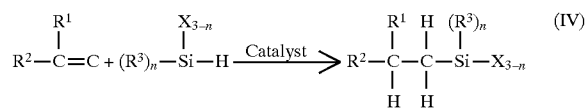

The conversion of the vinylidene double bond to a single bond and formation of a carbon-silicon bond between the carbon previously having the vinylidene double bond in the vinylidene olefin and the silicon atom in the monomeric silane forms an ethylsilyl moiety extending from a hydrocarbon backbone divided into a first portion and a second portion. If other alkylsilyl moieties are desired, the alkylsilane would require additional alkyl or other groups extending from the silicon atom next to the silicon-hydrogen bond. The resulting branched alkylsilane is suitable for use in forming a treated substrate or for forming a bonded phase.

The reaction represented by formula (IV) may be carried out with an excess (preferably about 10 wt % excess) of the monomeric alkylsilane, however, this is not necessary. All, or optionally only a portion, of the monomeric alkylsilane is added to the vinylidene olefin, which is preferably in a liquid, more preferably a solvent, medium. The catalyst may be charged to the reaction mixture. The reaction mixture should then be heated to a temperature of from about 30° to 200° C., preferably from about 60° to about 160° C. under preferably substantially oxygen-free conditions. An exotherm, typically moderate, may occur, at which time, the remaining allylsilane, if not already added, should be added to the reaction mixture, while maintaining the temperature in the range stated above. If only a portion of the alkylsilane is added initially, the reaction mixture may be heated prior to addition of the catalyst, followed by later addition of the remaining alkylsilane. Preferably, all reactants, including the catalyst, are added simultaneously and the reaction mixture heated. It should be understood, based on this disclosure, that the reaction conditions may have to be adjusted for various monomeric silanes and vinylidene olefins which may have varied levels of reactivity and electronegativity.

Once the branched alkylsilane is formed, it may be used in various chromatographic applications. The branched alkylsilanes, preferably having at least one hydrolyzable group bound to silicon in the alkylsilyl moiety may be used to treat substrates comprising silicon, preferably materials such as silica. The substrates containing silicon atoms may be treated by suspending or dispersing the substrate material in a solvent or other liquid medium. If silica is used, it is preferred that the silica be relatively dry. The alkylsilane is added to the silica/liquid medium and the silica and alkylsilane are reacted in the presence of an amine, such as pyridine, in order to initiate reaction with a hydroxyl-containing support, such as silica. The resulting Si—O—Si bond provides the point of attachment between the substrate and the branched alkylsilane. Specific reaction mechanisms which may be used for attaching the branched alkylsilanes of the invention to silica to form a treated substrate are described in P. Van Der Voort et al., *J. Liq. Chrom. & Rel. Technol.*, 19 (17&18),p.2743–2752 (1996) which is incorporated herein by reference.

These reactions can be modified for other substrate types or for various alkylsilyl moieties, however, it is preferred that the hydrolyzable group(s) bound to the silicon atom in the alkylsilyl moiety be capable of reacting with a hydroxy group to leave oxygen attached to the silicon atom to link it to the substrate.

The treated substrate having the branched alkylsilane attached to the substrate surface as described above may be used as a bonded phase in chromatographic applications. A bonded phase may be formed by preparing a branched alkylsilane as described above and reacting the branched alkylsilane with a substrate comprising silicon in the presence of a hydroxy-containing compound to form a Si—O—Si bond between the silicon of the alkylsilyl moiety and the silicon of the substrate as described above. Once the treated substrate is formed, it must be separated from the solvent or other liquid medium for use as a bonded phase. Filtering or other typical purification means may be used.

The present invention by providing a high degree of interaction, but using an asymmetric structure extending from the substrate, minimizes the effects of chain folding and limits the potential for crystallization. The branching of the hydrocarbon portions of the alkylsilane isolates and protects the linking bonds between the alkylsilane and the substrate, protecting them from hydrolytic attack and minimizing the effects of chain folding in the bonded phase. Further, by starting with shorter olefin chains and acquiring increased interaction capability by virtue of the dimerized structure of the vinylidene olefin reactant, the resulting alkylsilanes have a high degree of purity and can be formed from a simple synthesis reaction without the purity problems encountered in forming high molecular weight α-olefins chains.

The invention will now be described in more detail with respect to the following, non-limiting examples:

EXAMPLE 1

Prior to preparing a branched alkylsilane according to the present invention, a vinylidene olefin was prepared. The vinylidene olefin prepared was a tetradecene dimer (octacosene). A 5-L-, 3-neck, round bottom flask was used which was equipped with a nitrogen bubbler protected condenser, a subsurface inlet for nitrogen sparging, a rubber septum and a magnetic stirrer. The flask was charged with 3 liters of 1-tetradecene and sparged with nitrogen for 16 hours. Under stringent oxygen-free conditions, 20 ml of triisobutylaluminum was added to the flask. The mixture was agitated and heated to 110° C. Upon heating, evolution of isobutylene was observed, and the temperature gradually increased to 200° C. by heating and maintaining the temperature for a period of time of 5 hours. The mixture was allowed to cool to room temperature and 300 ml of 10% sodium hydroxide were added to deactivate the catalyst. The organic layer was separated and washed three times with 300 ml of deionized water. The product was isolated by distillation under reduced pressure. The product was identified as 2-dodecylhexadec-1-ene (tetradecene dimer) having a boiling point of 96-8°/1 mm and a melting point of 23-4° C. The product weighed 1700 g for a yield of 73% and was isolated in 99% purity.

Once the vinylidene olefin was formed, the vinylidene olefin was used to prepare a branched alkylsilane in accordance with the invention. A 4L-autoclave was charged with 785 g of the 2-dodecylhexadec-1-ene formed as described above with 250 g of toluene, a 10% excess (416 g) of dimethylchlorosilane as the silane monomer, and, using a syringe, 1 ml of platinum-divinyltetramethyldisiloxane complex having 3 wt % platinum. The autoclave was heated to 140° C. under autogenous pressure and the reaction was maintained for 24 h. The resulting product was 13-(chlorodimethyl-silylmethyl)heptacosane having a boiling point of 230° C. at 0.05 mm, a density of 0.848 g/cm$^3$ at 25° C., a refractive index of 1.454 at 30° C. and a yield of 55%. The product maintained liquid behavior to below 0° C.

EXAMPLE 2

The branched alkylsilane reaction product of Example 1 having chlorine as a hydrolyzable group was further treated to provide a dialkylamino-hydrolyzable group in place of chlorine. A 3 L-, 3-neck round bottom flask equipped with a nitrogen bubbler protected dewar (Dry-ice) condenser having an addition funnel and a mechanical stirrer was used. The flask was charged with 486 g of 13-(chlorodimethyl-silylmethyl)heptacosane formed in Example 1 and 1000 ml heptane and warmed to 40° C. The addition funnel was charged with 2.2 equivalents of dirnethylamine. The addition immediately resulted in precipitation of white salts. After the addition was complete, the mixture was heated for 4 hours and allowed to cool. The mixture was then filtered and the solvent removed under vacuum leaving a filtrate reaction product of 13-(N,N-dirnethylaminodimethylsilylmethyl)heptacosane.

EXAMPLE 3

A 2 L, 3-neck round bottom flask equipped with a nitrogen bubbler protected condenser, an addition funnel, a rubber septum and a magnetic stirrer was used. The flask was charged with 450 g of 2-tetradecyloctadec-1-ene (hexadecene dimer) and 250 g of toluene. Approximately 25% of the trichlorosilane was added to the flask and the flask was heated to 70° C. Using a syringe, 1 ml of platinum-divinyl-tetramethyldisiloxane complex (3 wt % platinum) was added through the septum. After 5–15 minutes, a moderate exotherm was observed the balance of the trichlorosilane was added at a rate to maintain the temperature between 80° and 120° C. The product was stripped of volatiles at 150° C. at 0.5 mm. The resulting product was 15-(trichloro-silylmethyl)hentriacontane having a yield of 225 g (39%). The solid product was not distillable without degradation at vacuum of 0.01 mm. It formed a 60% solution in toluene (density was 0.695 g/cm$^3$).

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A branched alkylsilane, comprising a branched hydrocarbon backbone having a linear or branched alkylsilyl moiety extending asymmetrically from the backbone such that the backbone has a first portion extending at least six carbon atoms from the alkylsilyl moiety and a second portion extending from the alkylsilyl moiety, the second portion having two carbon atoms more than the first portion, wherein said alkylsilyl moiety comprises at lest one hydrolyzable group bound to silicon for reacting with a substrate.

2. The branched alkylsilane according to claim 1, wherein the first and second portions of the hydrocarbon backbone are aliphatic.

3. The branched alkylsilane according to claim 1, wherein the alkylsilyl moiety is an ethylsilyl group.

4. The branched alkylsilane according to claim 1, wherein the at least one hydrolyzable group is selected from the group consisting of halogen, alkylamine, dialkylamine, and alkoxy.

5. The branched alkylsilane according to claim 4, wherein the hydrolyzable group is selected from the group consisting of chlorine, and dimethylamine.

6. The branched alkylsilane according to claim 1, wherein the branched alkylsilane has the following formula:

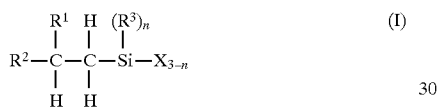

wherein $R^1$ is the first portion of the hydrocarbon backbone and is a substituted or unsubstituted alkyl chain of m carbon atoms; m being an integer such that $18 \geq m \geq 6$; $R^2$ is the second portion of the hydrocarbon backbone and is a substituted or unsubstituted alkyl chain of m+2 carbon atoms; $R^3$ is a substituted or unsubstituted linear or branched alkyl chain of from 1 to 4 carbon atoms; n is from 0 to 2; and X is a group selected from the group consisting of alkyl, halogen, alkylamine, dialkylamine, and alkoxy.

7. The branched alkylsilane according to claim 1, wherein the branched alkylsilane is formed by the hydrosilylation reaction of a vinylidene olefin and a monomeric silane in the presence of a metallic catalyst.

8. A branched alkylsilane, comprising a branched aliphatic hydrocarbon backbone having a linear or branched alkylsilyl moiety extending asymmetrically from the backbone such that the backbone has a first portion and a second portion extending from the alkylsilyl moiety, the second portion having two carbons more than the first portion, wherein said alkylsilyl moiety comprises at least one hydrolyzable group bound to silicon for reacting with a substrate, and the branched alkylsilane has formula (1):

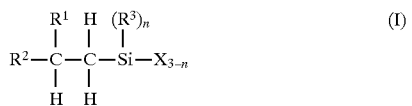

wherein $R^1$ is the first portion of the hydrocarbon backbone and is a substituted or unsubstituted alkyl chain of m carbon atoms; m being an integer such that $18 \geq m \geq 6$; $R^2$ is the second portion of the hydrocarbon backbone and is a substituted or unsubstituted alkyl chain of m+2 carbon atoms; $R^3$ is a substituted or unsubstituted linear or branched alkyl chain of from 1 to 4 carbon atoms; n is from 0 to 2; and X is a group selected from the group consisting of alkyl, halogen, alkylamine, dialkylamine, and alkoxy.

9. A treated substrate for use in chromatographic applications, comprising a substrate and a branched alkylsilane comprising a branched hydrocarbon backbone having a linear or branched alkylsilyl moiety extending asymmetrically from the backbone such that the backbone has a first portion and a second portion extending from the alkylsilyl moiety, the second portion having two carbon atoms more than the first portion, wherein silicon in the alkylsilyl moiety is bound to the substrate by an oxygen atom such that the first portion and the second portion of the backbone extend outwardly from the substrate for providing a treated substrate useful for reproducible molecular interaction.

10. The substrate according to claim 9, wherein the substrate comprises silica, and the silicon in the branched alkylsilyl moiety and silicon in the substrate form an Si—O—Si bond.

11. A method for preparing a branched alkylsilane useful for chromatographic applications, comprising the steps of:
(a) preparing a vinylidene olefin by dimerization of an α-olefin;
(b) reacting the vinylidene olefin and a monomeric silane having a silicon-hydrogen bond in the presence of a metallic catalyst such that the silicon-hydrogen bond is added to a vinylidene double bond in the vinylidene olefin thereby, converting the vinylidene double bond to a single bond and bonding the silicon of the monomeric silane to the vinylidene olefin to form a branched alkylsilane having a first portion and a second portion extending from an alkylsilyl moiety, the second portion having two carbon atoms more than the first portion.

12. The method according to claim 11, further comprising providing at least one hydrolyzable group to the monomeric silane such that the resulting branched alkylsilane comprises the at least one hydrolyzable group for use in bonding the branched alkylsilane to a substrate.

13. The method according to claim 11, wherein step (a) further comprises contacting an α-olefin having at least 8 carbon atoms with a suitable olefin polymerization catalyst to form the vinylidene olefin, neutralizing the catalyst, and purifying the reaction product.

14. The method according to claim 13, wherein the α-olefin is selected from the group consisting of alkenes of from 8 to 20 carbon atoms.

15. The method according to claim 14, wherein the α-olefin is selected from the group consisting of 1-dodecene, 1-hexadecene, and 1-tetradecene.

16. The method according to claim 11, wherein the metallic catalyst is selected from the group consisting of platinum-divinyltetramethylsiloxane complex, platinum-cyclovinylmethylsiloxane complex, chloroplatinic acid, chloroplatinic acid complexes, chloroplatinic acid solutions, and tris-triphenyl phosphine rhodium chloride.

17. A method for forming a bonded phase for use in chromatographic applications, comprising
(a) forming a branched alkylsilane comprising a hydrocarbon backbone and a linear or branched alkylsilyl moiety having at least one hydrolyzable leaving group bound to silicon and extending asymmetrically from the backbone such that the backbone has a first portion and a second portion extending from the alkylsilyl moiety, the second portion having two carbon atoms more than the first portion; and (b) reacting the branched alkylsilane with a substrate comprising silicon in the presence of a hydroxy-containing compound to form a Si—O—Si bond between the silicon of the alkylsilyl moiety and the silicon of the substrate.

18. The method according to claim 17, wherein step (b) further comprises reacting the branched alkylsilane and substrate in a solvent solution and the method further comprises separating the substrate from the solvent solution.

19. The method according to claim 17, wherein step (a) further comprises hydrosilylation of a vinylidene olefin with an alkylsilane in the presence of a metallic catalyst.

* * * * *